United States Patent [19]

Ando et al.

[11] Patent Number: 4,560,273

[45] Date of Patent: Dec. 24, 1985

[54] METHOD AND APPARATUS FOR INSPECTING PLATED THROUGH HOLES IN PRINTED CIRCUIT BOARDS

[75] Inventors: Moritoshi Ando, Atsugi; Kikuo Mita, Yokohama; Yoshikazu Kakinoki, Machida, all of Japan

[73] Assignee: Fujitsu Limited, Kawasaki, Japan

[21] Appl. No.: 554,543

[22] Filed: Nov. 23, 1983

[30] Foreign Application Priority Data

| Nov. 30, 1982 | [JP] | Japan | 57-210110 |
| Dec. 27, 1982 | [JP] | Japan | 57-228369 |
| Dec. 27, 1982 | [JP] | Japan | 57-228375 |
| Dec. 27, 1982 | [JP] | Japan | 57-228376 |
| Dec. 28, 1982 | [JP] | Japan | 57-228672 |
| Dec. 28, 1982 | [JP] | Japan | 57-228673 |
| Dec. 28, 1982 | [JP] | Japan | 57-228676 |
| Jan. 28, 1983 | [JP] | Japan | 58-11394 |
| Jan. 28, 1983 | [JP] | Japan | 58-11395 |
| Jan. 28, 1983 | [JP] | Japan | 58-11396 |

[51] Int. Cl.[4] .......................... G01N 21/88
[52] U.S. Cl. .................. 356/237; 356/239; 356/241
[58] Field of Search ................. 356/237, 239, 241

[56] References Cited

U.S. PATENT DOCUMENTS

| 3,698,821 | 10/1972 | Ekstrand | 356/237 |
| 4,145,714 | 3/1979 | MacDonald et al. | 356/106 |
| 4,302,105 | 11/1981 | Sick | 356/237 |
| 4,447,152 | 5/1984 | Rainford et al. | 356/237 |

Primary Examiner—John E. Kittle
Attorney, Agent, or Firm—Staas & Halsey

[57] ABSTRACT

In inspecting plated through holes in printed circuit boards, light from a light source is introduced into the light conducting substrate of the printed circuit boards having through holes. A light detector senses the light in the holes. The detected through holes are masked to prevent the light from entering the through hole of the substrate. A light detector senses light leaked to the hole. By signals supplied from the light detectors, the plated through holes can be continuously and efficiently inspected.

33 Claims, 32 Drawing Figures

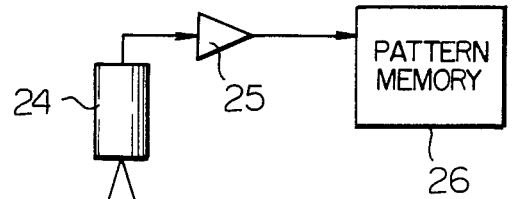
Fig. 3A
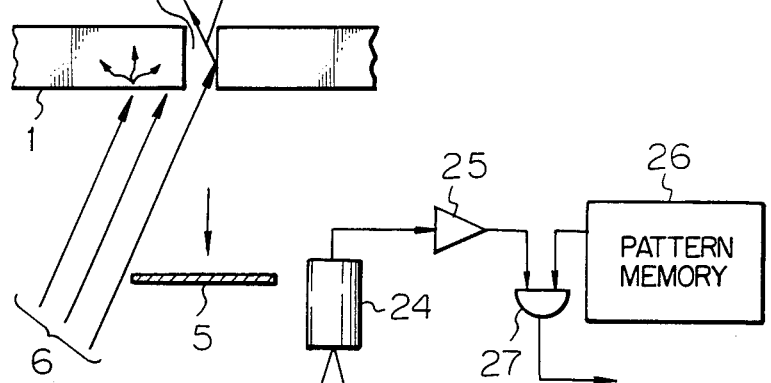
Fig. 3B
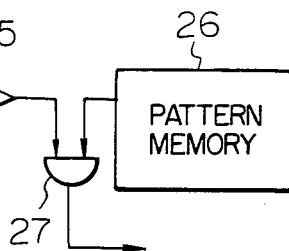
Fig. 3C
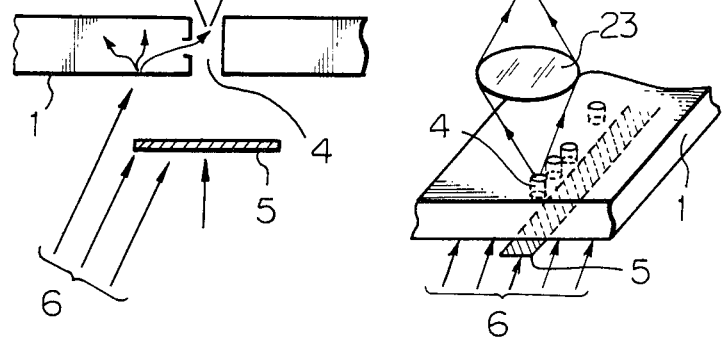

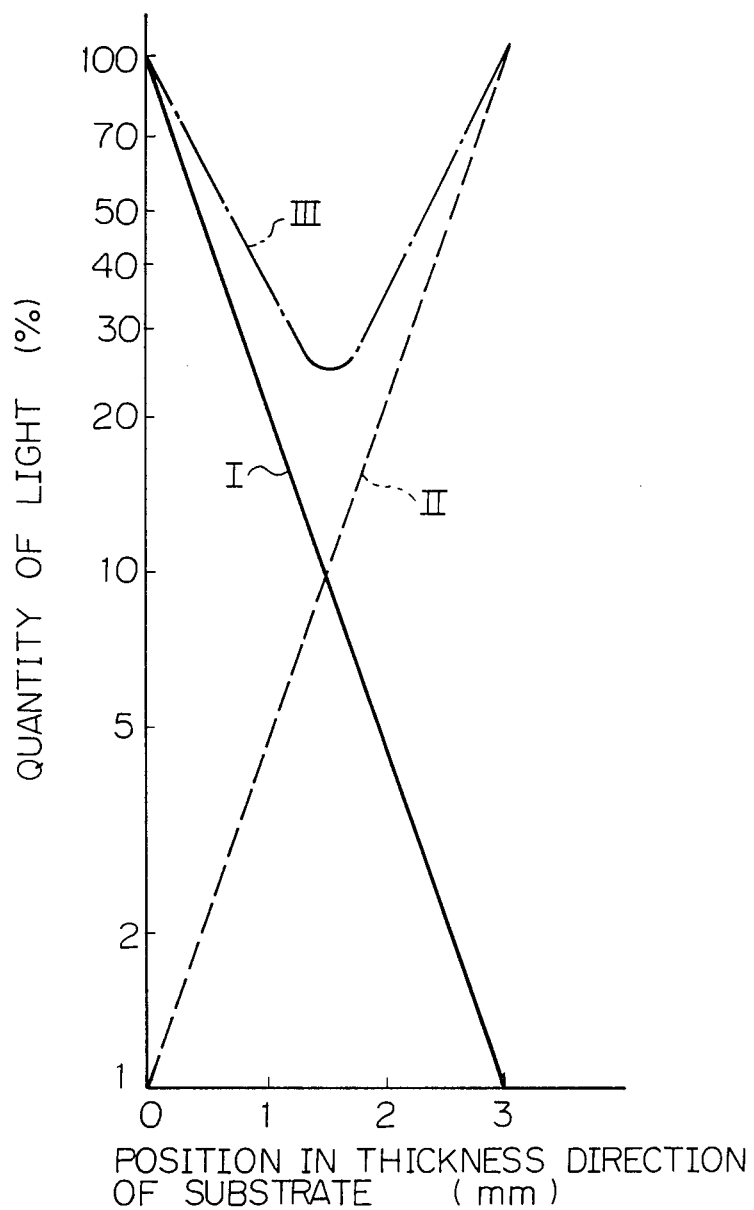

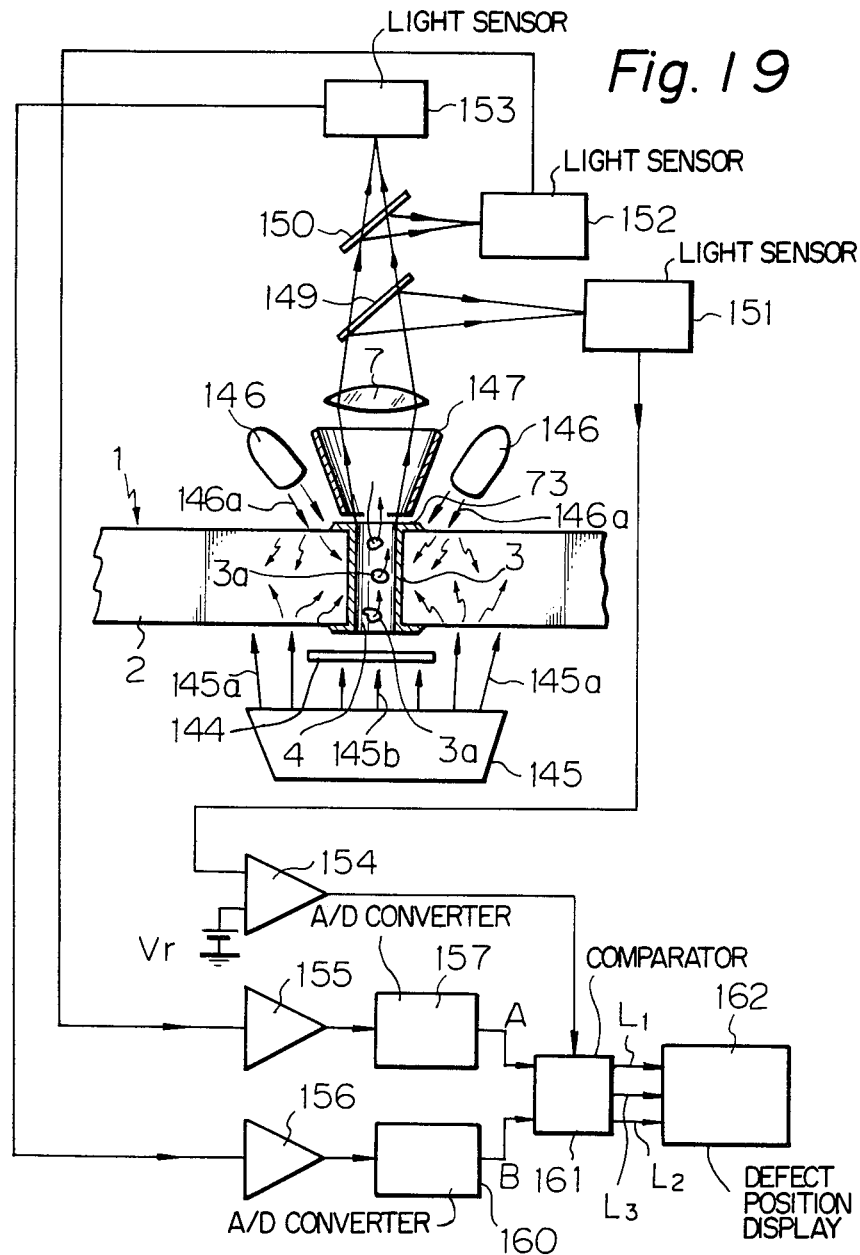

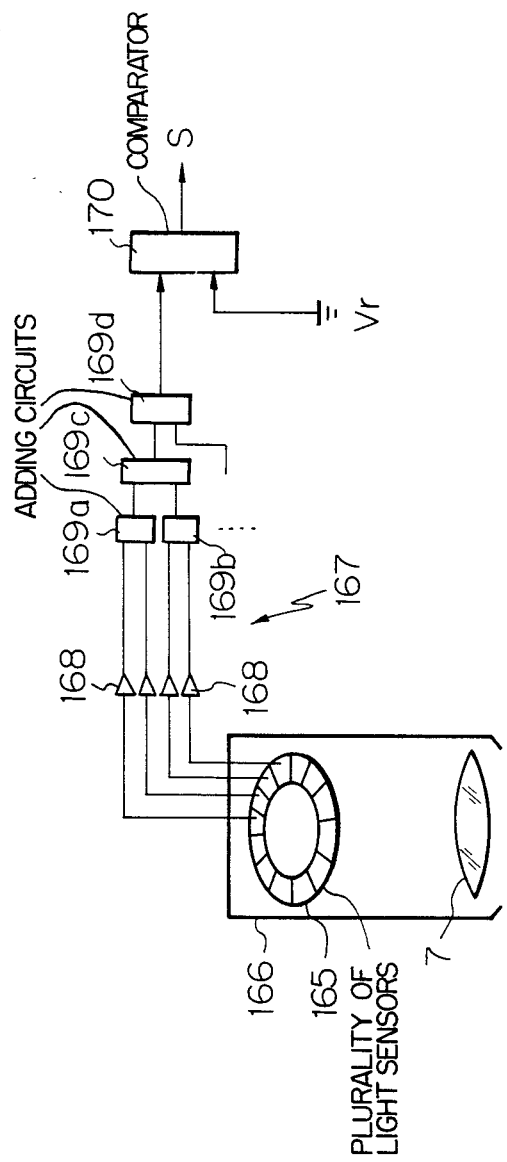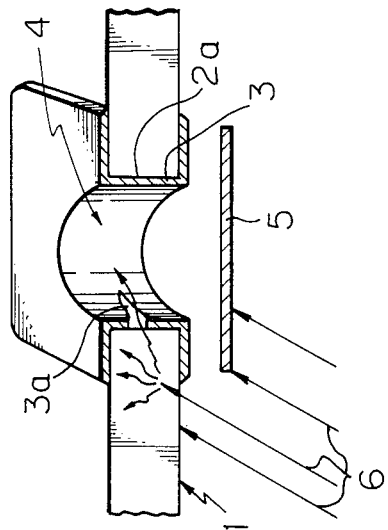
Fig. 20

METHOD AND APPARATUS FOR INSPECTING PLATED THROUGH HOLES IN PRINTED CIRCUIT BOARDS

BACKGROUND OF THE INVENTION

1. Field of the Invention

The present invention relates to a method and apparatus for inspecting plated-through holes in printed circuit boards, more particularly, to a new and improved method and apparatus for inspecting plated through holes in circuit boards wherein a light source is used to aid in the inspection process.

2. Description of the Prior Art

A through-hole plating method is commonly used for connecting a surface conductor to a back side conductor of a double-sided board and for interlayer connecting a multilayer printed circuit board.

The through-hole plating method comprises the steps of forming a through hole in conductor-laminated insulating substrates and chemically or electrically forming a plated layer on the inner wall of the through hole to connect the laminated conductors to each other.

Since the plated layer generally has a thickness on the μm order, the plated layer of the inner wall of the through hole often suffers from pinholes, cracks, or other defects. Too large a defective portion of the plated layer results in poor electrical connection of the conductors and deteriorates the reliability of the printed circuit boards. Therefore, inspection of the through holes is required.

The inspection of plated through holes in printed circuit boards has, as a general practice, been effected either manually or electrically. Manual inspection is accomplished through the utiliization of a microscope. This, however, requires individual inspection of each through hole, which is both time consuming and very fatiguing to the inspector. The smaller the through-hole diameter, the greater the time consumed and the greater the fatigue.

Electrical inspection is accomplished, for example, through the method and apparatus for inspecting plated through holes as described in U.S. Pat. No. 3,698,821, granted on Oct. 17, 1972. In the above U.S. patent, there is provided a method and apparatus utilizing a light source for inspecting plated through holes in printed circuit boards comprising means for introducing light from the source into the interior of the printed circuit board and preventing light from directly entering the plated through holes in the board. Also provided is means for detecting the presence of light within a plated through hole in the board, the detected light entering the hole through a defectively plated wall of the hole from the interior of the printed circuit board.

The method and apparatus of U.S. Pat. No. 3,698,821 enables reliable inspection of defective portions of a through hole, however, in this invention the through holes cannot be easily located at the inspecting position. Only when the location of the through hole is found, can the method and apparatus be efficiently used.

SUMMARY OF THE INVENTION

An object of the present invention is to provide a method and apparatus for efficiently inspecting through holes by detecting signals indicating the location of the through holes and signals indicating the defective portions.

A further object of the present invention is to provide an apparatus for efficiently and continuously inspecting through holes by using a mask.

A still further object of the present invention is to provide an apparatus for inspecting through holes wherein the radiation system of light rays is simplified.

A further object of the present invention is to provide an apparatus for inspecting through holes having a large aspect ratio. The aspect ratio R is defined by the equation $$R = b/a,$$

wherein a is the diameter of the through hole and b is the thickness of the printed board.

A still further object of the present invention is to provide an apparatus for inspecting through holes wherein control of the optical system for condensing light can be simplified.

A still further object of the present invention is to provide an apparatus for inspecting through holes which can be installed in a small space.

A still further object of the present invention is to provide an apparatus for inspecting through holes wherein the distribution of light in the substrate is substantially equalized.

A still further object of the present invention is to provide an apparatus for inspecting through holes, wherein the location of defective portions of the through holes can be detected.

A still further object of the present invention is to provide an apparatus for inspecting through holes wherein the shape of the defective portion in the through holes can be found and wherein permissible and unpermissible through holes can be found.

According to the present invention, there is provided an apparatus utilizing a source of light for inspecting plated through holes in printed circuit boards made of conducting material. The apparatus includes a masking means for introducing light from the source into the interior of the printed circuit board, the masking means preventing light from directly entering the plated through holes in the board. There is also provided means for detecting the presence of the plated through holes, means for detecting the presence of light within plated through holes in the board, the detected light entering the holes through defectively plated walls of the through holes from the interior of the printed board, and means for judging the presence of defectively plated walls of the through holes in response to signals from the means for detecting the presence of the plated through holes and the means for detecting the presence of light within plated through holes in the board.

According to the present invention there is further provided an apparatus, utilizing a source of light for inspecting plated through holes in printed circuit boards made of light conducting material, includes masking means for introducing light from the sources into the interior of the printed circuit board, the masking means being located at both sides of the printed circuit board and preventing light from directly entering the plated through holes in the board, the source of light being located at both sides of the printed circuit board, and respective light from the source located at both sides of the printed circuit board having different wavelengths. The apparatus further includes means for detecting the presence of the plated through holes, means for detecting the presence of the respective light within the plated through holes in the board, the detected light entering the holes through defectively plated walls of the holes from the interior of the board, and means for judging the position of defectively plated walls of the plated through holes connected to means for detecting the presence of the respective light within the plated through holes in the board. Further, according to the present invention, there is provided an apparatus, utilizing a source of light for inspecting plated through holes in printed circuit boards made of light-conducting material, includes masking means for introducing light from the source into the interior of the printed circuit board, the masking means preventing light from directly entering the plated through holes in the board, means for detecting the presence of said plated through holes, and means for detecting the image of light within plated through holes in the board, the detected light entering the holes from the interior of the printed circuit board. The apparatus further includes, connected to the means for detecting the image of the plated through holes and the means for detecting the presence of light within plated through holes in the board, for judging the degree of the defects in the defectively plated walls of the through holes.

Futhermore, according to the present invention, there is provided a method of inspecting printed circuit boards made of light-conducting material for detecting defective plated through holes, which includes the steps of introducing light into the printed circuit board, and confirming the presence of the plated through holes by detecting light withhin the plated through holes to obtain a display signal indicating the presence of holes. The method further includes detecting the presence of light within plated through holes to obtain display signals indicating the presence of defectively plated walls of the holes, the light of the through holes arriving through defectively plated walls of the holes, and displaying a defect signal by replying to the display signal of indicating presence of the plated-through hole and the display signal indicating the presence of a defectively plated wall of the through hole.

Still further, according to the present invention there is provided a method of inspecting a printed circuit board made of light-conducting material for detecting defectively plated through holes, including the steps of introducing light into the printed circuit board, confirming the presence of the plated through holes by detecting the light within the plated through holes to obtain a display signal of the presence of the through holes, and masking the plated through holes with an opaque material. The method further includes detecting the presence of light within plated through holes, the light entering the holes through defectively plated walls of the holes, and displaying a defect signal by replying to the display signal indicating the presence of the plated-through hole and the display signal indicating the presence of a defectively plated wall of the through hole.

BRIEF DESCRIPTION OF THE DRAWINGS

FIGS. 3A and 3B are schematic cross-sectional diagram and FIG. 3C is a perspective view of the mask which is capable of moving upward and downward;

FIG. 17 is a graph of the relationship between the quantity of light and the position in the thickness direction of a substrate;

FIG. 19 is a schematic cross-sectional diagram of a fifth embodiment according to the present invention;

FIG. 20 is a schematic diagram of a sixth embodiment according to the present invention;

DESCRIPTION OF THE PREFERRED EMBODIMENTS

Figure 1:
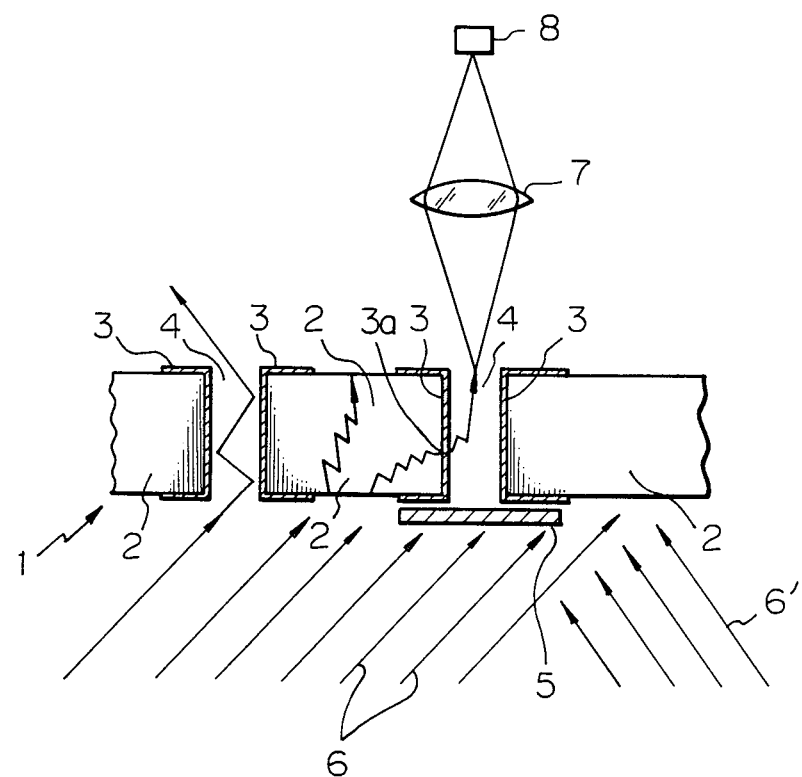
FIG. 1 is a schematic cross-sectional diagram for explaining the principle of detecting the presence of a through hole and a defectively plated wall of a through hole.

FIG. 1 is a schematic cross-sectional diagram for explaining the principle of detecting the presence of a through hole and a defectively plated wall of a through hole. In FIG. 1, a printed circuit board 1 has through holes 4 formed in a light-conducting substrate 2 such as a material composed of glass fibers which are impregnated with epoxy resin. The through holes 4 have conductive layers 3 on the inner walls thereof. An opaque body 5, hereinafter referred to as a mask, is positioned on the lighting side (light 6 and 6') to be spaced from the printed circuit board 1 at a predetermined distance, for example, 0.1 mm. Reference numeral 7 denotes a lens and reference numeral 8 a light sensor.

Using the above-mentioned apparatus, defects 3a in the through holes 4 can be detected by lens 7, light sensor 8, and mask 5 are first positioned at the location of the through hole 4 to be inspected. Light rays 6 and 6' from a light source (not shown) are obliquely radiated at the region of the printed circuit board 1 where the mask 5 shields the through hole 4. If there is a defect 3a in the conductive layer 3, the light rays passing through the light-conducting substrate 2 to the wall of through hole 4 come through the defect 3a. By detecting the light rays emerging from the defect 3a by the light sensor 8 through the lens 7, defects 3a of the conductive layer 3 of the through hole 4 can be easily detected.

Since the mask 5, made of, for example, felt 2 mm wide and 4 mm long, is spaced apart from the substrate 2 at a predetermined distance of 0.1 to 1 mm, there can be provided means for relative movement between the mask 5 and the printed circuit board 1 to enable speedy detection of defects 3a.

Figure 2:
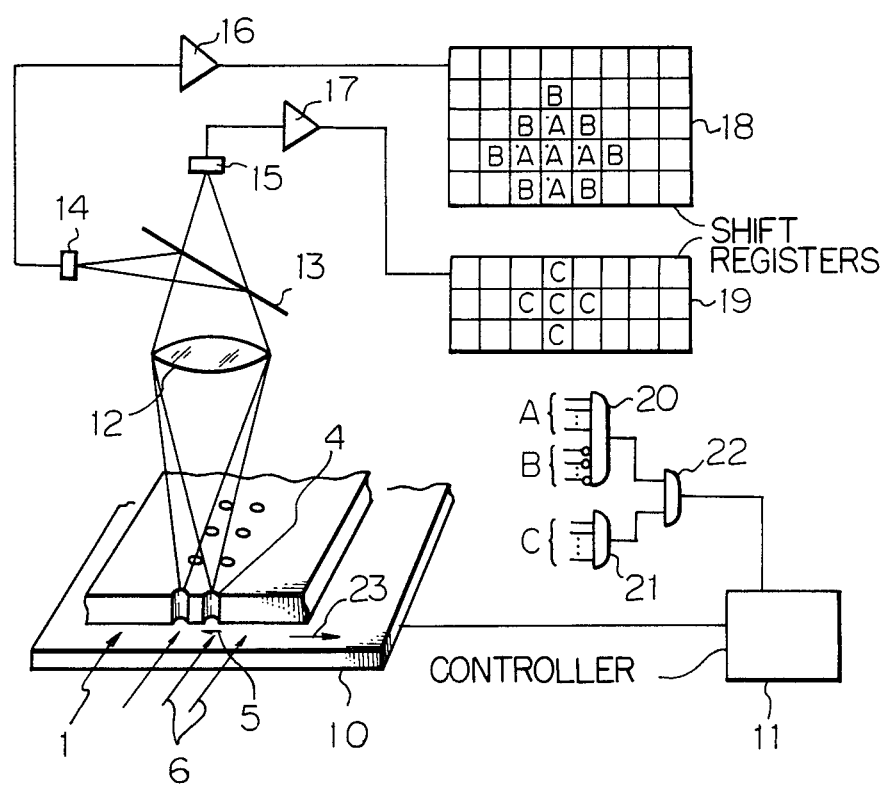
FIG. 2 is a schematic diagram of a first embodiment according to the present invention.

FIG. 2 is a cross-sectional view of a first embodiment of the present invention. In this figure, reference numerals the same as in FIG. 1 denote the same elements. A stage 10 is driven and controlled by a controller 11. A lens 12 and a half mirror 13 form an optical device system. A light sensor 14 inspects direct light rays from a preceding through hole 4 in the direction of movement of the stage 10 on which the printed circuit board is arranged. A light sensor 15 inspects light rays emerging from a through hole 4 shielded by the mask 5. These light sensors 14 and 15 are respectively connected to shift registers 18 and 19 through corresponding digitizing circuits 16 and 17.

The shift registers 18 and 19 have a sufficient capacity to include a region corresponding to the position differences detected by the light sensors 14 and 15.

Further, in the shift registers 18 and 19 for the printed circuit board 1, position output bits A and B are supplied to an AND gate 20. Position output bits C are supplied to an AND gate 21. The output of these AND gates 20 and 21 are connected to the controller 11 through an AND gate 22.

The operation of the embodiment will be explained below. Light rays 6 are radiated obliquely toward the underside of the printed circuit board 1. At the same time, the stage 10 is moved in a predetermined direction, for example, the direction of arrow 23, under the control of the controller 11. During the movement of the stage 10, the direct light rays 6 from the through hole 4 are detected by the detecting apparatus system consisting of the lens 12, half mirror 13, and light sensor 14. Thus, an analog through-hole position indication signal can be obtained. The analog signal is digitized by the digitizing circuit 16 and is transmitted to the shift register 18 in synchronization with the above movement of the printed circuit board 1.

When the stage 10 is moved so that the through hole 4 is inspected by the detecting apparatus system consisting of the lens 12 and the light sensor 15, a defect indication signal occurs. This signal is digitized by the digitizing circuit 17 and is transmitted to the shift register 19 in synchronization with the above movement of the printed circuit board 1.

The defect indication signal transmitted to the shift register 19 appears as a predetermined output of the shift register 19 at the completion of the transmission thereof or after a predetermined period of time. At the same time, a through-hole position-indication signal previously transmitted to the shift register 18 also appears as a predetermined output of the shift register 18. The relationship between the outputs of the shift register 18 is diagrammatically shown in FIG. 2 as A and B and the relationship between the output of the shift register 19 is diagrammatically shown in FIG. 2 as C.

The output bits A and B supply the through-hole position-indication signal to the AND gate 20, while the output bits C supply the defect indication signal to the AND gate 21. Thus, a defect signal which shows whether defects 3a are present or not in the conductive layer 3 of the through hole 4 is generated from the AND gate 22 connected to the AND gates 20 and 21 and is supplied to the controller 11 to control the next process.

FIGS. 3A to 8B are cross-sectional or perspective views for explaining examples of masks according to embodiments of the present invention.

FIGS. 3A and 3B show a mask 5 which is capable of moving upward and downward. According to this example, when the mask 5 is away from the printed circuit board, the through-hole position-indication signal can be obtained as shown in FIG. 3A. On the other hand, when the mask 5 is near the printed circuit board 1, the defect indication signal can be obtained as shown in FIG. 3B. FIG. 3C is a perspective view of FIG. 3B.

Light rays 6 unhindered by the mask 5 are condensed by a lens 23 through the through hole 4, received by a TV camera 24, and converted to an electric signal. The electric signal is digitized by a digitizing circuit 25 and is recorded in a pattern memory 26 as a through-hole position-indication signal. After that, the mask 5 is drawn near the printed circuit board 1, so that the light rays 6 reaching the inner portion of the through hole 4 are not direct light rays, but only light rays from defects of the conductive layer 3 of the through hole 4.

When light rays from the defects 3a are present, a defect indication signal is supplied to one of two inputs of an AND gate 27 through the lens 23, the TV camera 24, and the digitizing circuit 25. At the same time, the through-hole position-indication signal read from the pattern memory 26 is supplied to the other input of the AND gate 27. Thus, a defect signal is output from the AND gate 27.

Figure 4A:
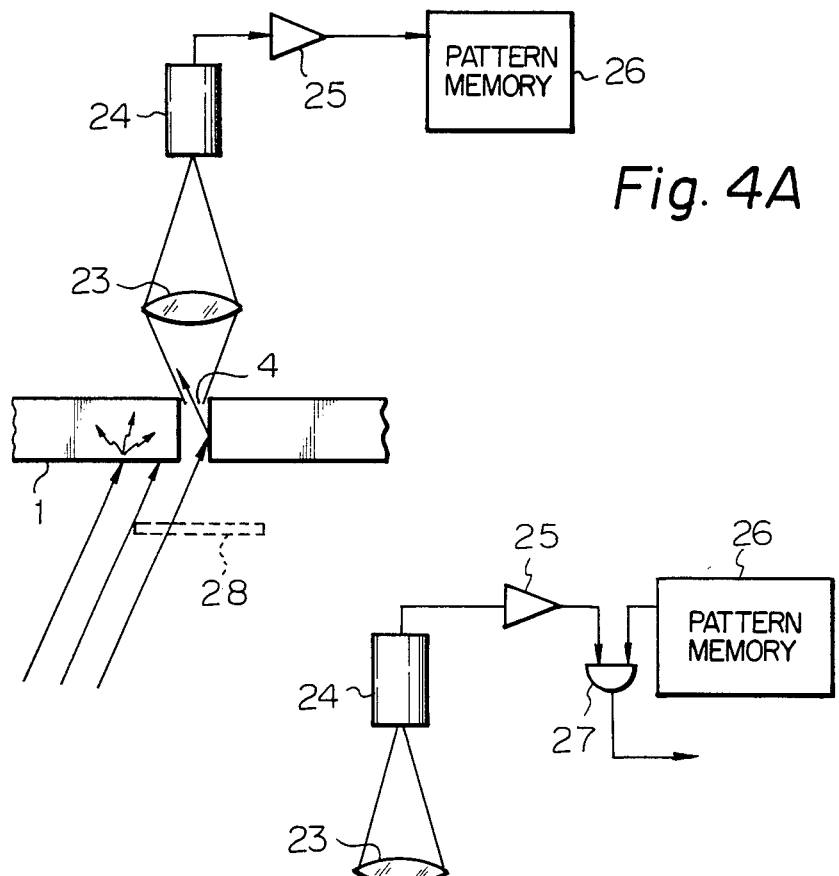
FIGS. 4A and 4B are schematic cross-sectional diagram of a mask composed of a liquid crystal.
Figure 4B:
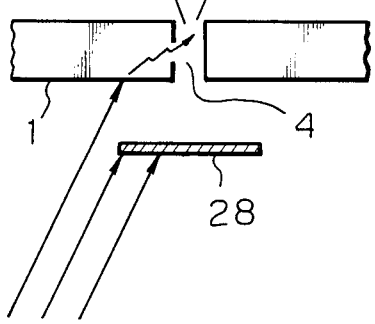

FIGS. 4A and 4B show a mask 28 composed of a liquid crystal mask. Use of a liquid crystal eliminates the need for movement of the mask.

Figure 5:
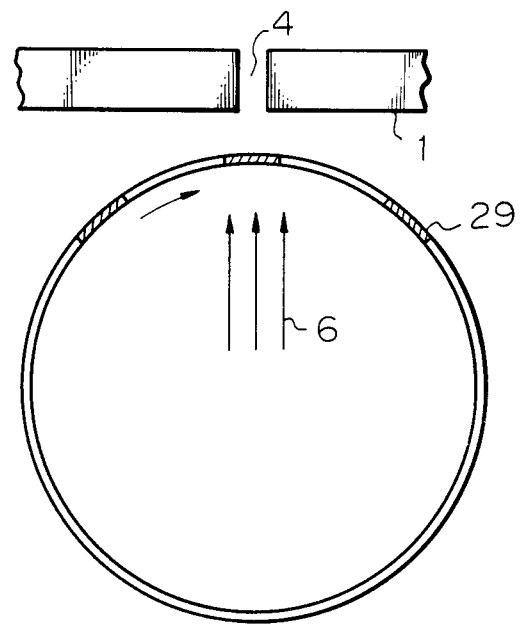
FIG. 5 is a schematic cross-sectional diagram of a cylindrical rotating mask.
Figure 6:
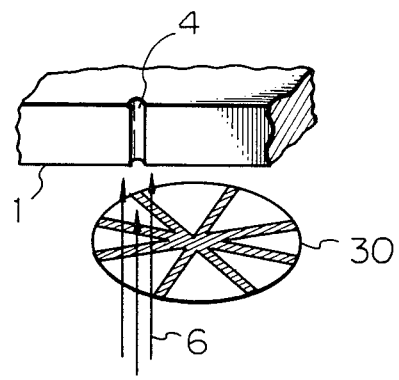
FIG. 6 is a perspective view of a rotating disk mask.

FIG. 5 shows a cylindrical rotating mask 29. FIG. 6 is a rotating disk mask 30.

Figure 7A:
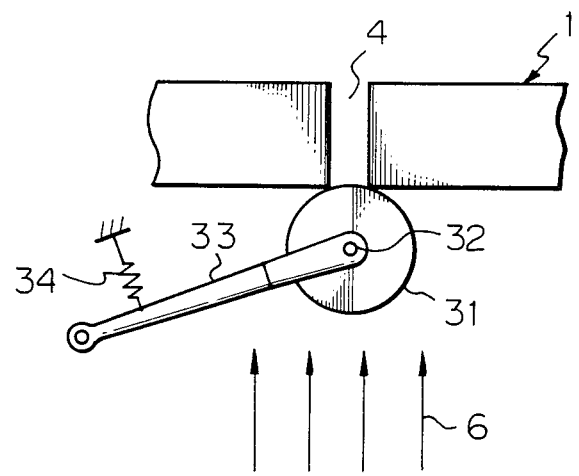
FIGS. 7A and 7B are diagrams of a roller mask.
Figure 7B:
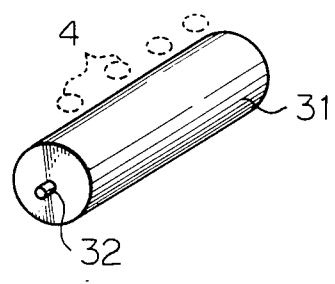

FIGS. 7A and 7B show a roller mask. In FIGS. 7A and 7B a roller body 31 for shutting off light from the through hole 4 is arranged at the lighting side of the printed circuit board 1. The roller body 31 has a length such that it can shut off light for a plurality of through holes, as shown in FIG. 7B. The ends of a support shaft 32 are supported by an arm 33 rotatably installed on a fixed portion. The roller body 31 is kept in close contact with the lighted surface of the printed circuit board 1 by a spring 34 installed between the arm 33 and the fixed portion.

With the above arrangement, light can be shut off from a plurality of through holes 4 by the roller body 31. Thus, it is not necessary to individually position masks for each through hole, resulting in improved inspection efficiency. In such case, the light sensor composed of a charge coupled Device (CCD) or line sensor, disposed above the other side of the printed circuit board 1 opposite the roller body 31, can detect many through holes at a time corresponding to the number of through holes shielded by the roller body 31.

Figure 8A:
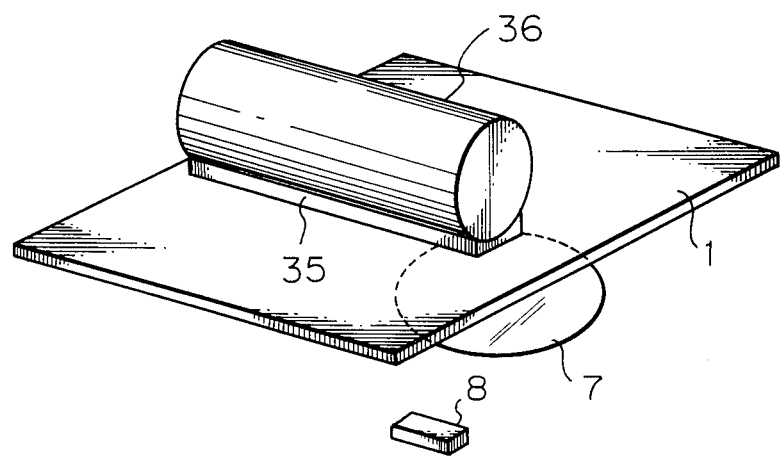
FIG. 8A is a perspective view of a mask adhered to a light source.
Figure 8B:
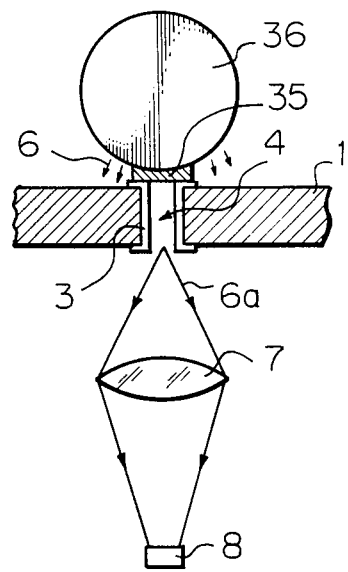
FIG. 8B is a schematic cross-sectional view of FIG. 8A.

FIG. 8A shows a mask adhered to the light source. FIG. 8B is a schematic cross-sectional view of FIG. 8A.

In FIG. 8A, a mask comprising 2.3 mm wide, 200 mm long, black rubber 35 is adhered to a light source 36, such as a fluorescent lamp, and covers the opening of the through hole (not shown). The light sensor 8, for example, a charge coupled device (CCD), is provided on the other side of the printed circuit board 1.

Referring to FIG. 8B, light rays 6 from the light source 36 pass through the printed circuit board 1. Part of the light rays 6 come out of defects of the conductor layer 3 and can be detected as leaked light rays 6a by the light sensor 8 through the lens 7.

Since the mask is previously adhered to the light source, the holder of the mask becomes simple and no control of the relative position of the light source and mask is needed. Thus, the light system can be simplified. Further, since a light source and mask having a rectangular cross-section, such as a strip, are used, a plurality of through holes over a wide area of the printed circuit board can be inspected at a predetermined position.

Figure 9:
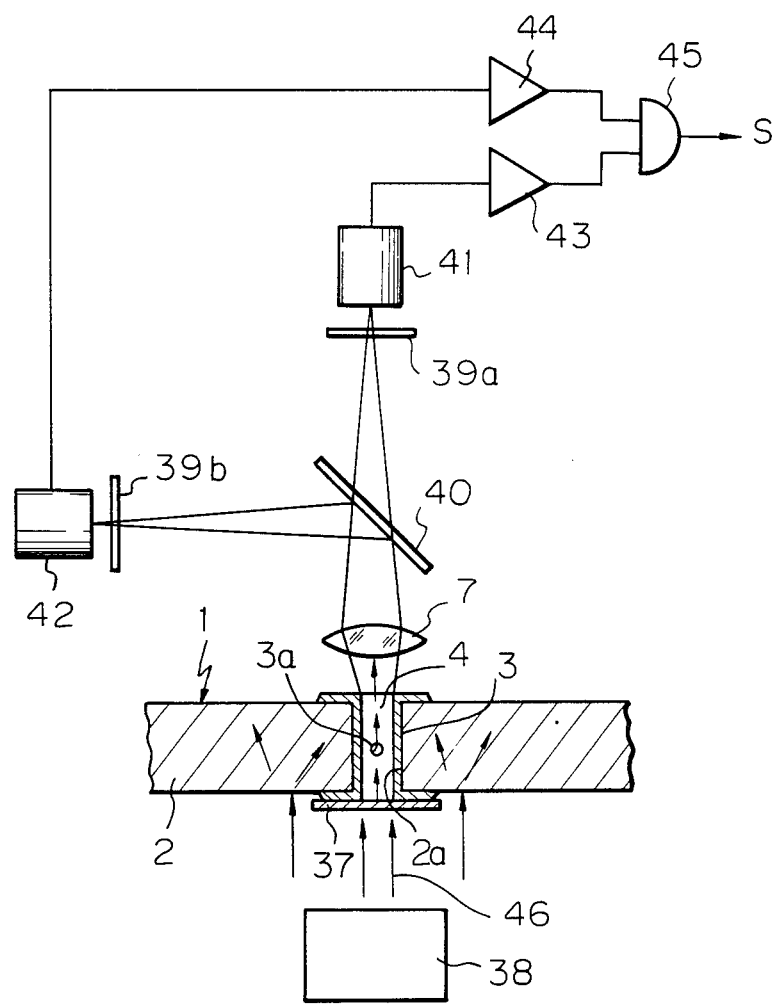
FIG. 9 is a schematic cross-sectional diagram of a second embodiment according to the present invention using masking means composed of a filter.

FIG. 9 is a a second embodiment according to the present invention. In FIG. 9, a filter 37, which closes one opening of the through hole 4 is provided as a mask at one side of the printed circuit board 1. The filter 37 passes light rays having a predetermined wavelength, for example, a green light ray. Further, at the side of the filter 37, there is provided a light generating device 38 which generates light rays which pass through the filter 37, for example, green light rays, and light rays which do not pass through the filter 37, for example, red light rays.

At the other side of the printed circuit board 1, opposite to the filter 37 and the light device 38, there is provided a lens 7. On the light axis of the lens 7 there is provided a half mirror 40, a filter 39a which passes only green light rays, and a light sensor 41 which detects the existence and position of the through hole 4. On the axis of light reflected by the half mirror 40, there is provided a light sensor 42 which detects defects of the through hole 4 through a filter 39b which passes only red light rays. Comparators 43 and 44 are connected to the output side of the light sensors 41 and 42, respectively.

When the light sensor 41 or 42 detects the position or existence of defects of the through hole 4, these comparators 43 and 44 output a "1". The output of comparators 43 and 44 are input to an AND circuit 45. When the logic condition of the AND circuit 45 is satisfied, the AND circuit 45 transmits a defect signal S.

The operation of the apparatus shown in FIG. 9 will be explained below. When one of the through holes 4 is indexed to the inspecting position, green and red light rays 46 are radiated from the light device 38 to the under surface of the printed circuit board 1. The green light rays pass through the filter 37 masking the through hole 4 and reach the lens 7 through the through hole 4. The passed green light rays are condensed and projected to the filter 39a through the half mirror 40 and, at the same time, are reflected by the half mirror 40 and projected to the filter 39b.

Since the filter 39b does not pass green light rays, the light sensor 42 is not operated. On the other hand, since the filter 39a passes green light rays, the green light rays are detected by the light sensor 41, with the result that the existence and position of the through hole 4 at the indexed position can be detected. The detected signal is supplied to the comparator 43, and the output of the comparator 43 is set to "1".

When red light rays are radiated from the light device 38 to the under surface of the printed circuit board 1, the red light rays enter the light-conducting substrate 2 and are diffused. If no defects 3a such as pinholes are present in the conductive layer 3, the diffused light rays do not leak to the through hole 4 and the light sensor 42 is not operated.

When the defect 3a is present in the conductive layer 3, however, the diffused red light rays in the light-conducting substrate 2 leak to the through hole 4. The leaked light rays are condensed by the lens 7 and transmitted to the filter 39a and the half mirror 40 where the light rays are also reflected to the filter 39b. Since the filter 39a does not pass red light rays, the light sensor 41 is not operated. On the other hand, since the filter 39b passes red light rays, the red light rays are detected by the light sensor 42 and the detected signal is supplied to the comparator 44 with the result that when the conductive layer 3 of the through hole 4 indexed to the inspecting position has defects, the output of the comparator 44 becomes "1". When both outputs of the comparators 43 and 44 become "1", the AND circuit 45 supplies high potential defect signals S, with the result that the defect 3a of the conductive layer 3 can be reliably detected.

When the through hole 4 is not positioned at the inspecting position or when the through hole 4 is significantly deviated in position from the inspecting position, even though the red light rays passing through the substrate 2 are detected by the light sensor 42, the high potential defect signal S is not supplied.

According to the embodiment of the present invention shown in FIG. 9, defects 3a of the conductive layer 3 of the through hole 4 can be reliably detected, the inspecting efficiency is improved, and the existence and position of the through hole 4 can be detected.

Figure 10A:
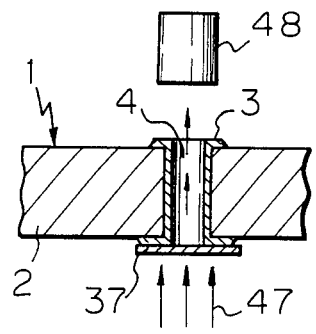
FIGS. 10A and 10B are schematic cross-sectional diagrams of another example of the embodiment shown in FIG. 9.
Figure 10B:
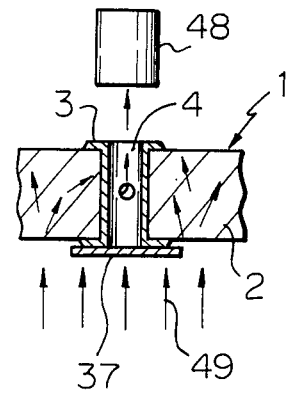

FIGS. 10A and 10B show another example of the embodiment shown in FIG. 9. As shown in FIG. 10A, one end of the through hole 4 is masked by the filter 37 which passes only green light rays. The under surface of the printed circuit board 1 is radiated from the filter 37 side by the green light rays 47. The green light rays which pass through the filter 37 are detected by a light sensor 48 positioned above the through hole 4 to detect the existence and the position of the through hole 4.

Then, as shown in FIG. 10B, the under surface of the printed circuit board 1 is radiated by red light rays 49 in place of green light rays. When the conductive layer 3 of the through hole 4 has a defect 3a, the diffused red light rays in the substrate 2 leak to the through hole 4. These leaked red light rays are detected by the light sensor 48.

Figure 11:
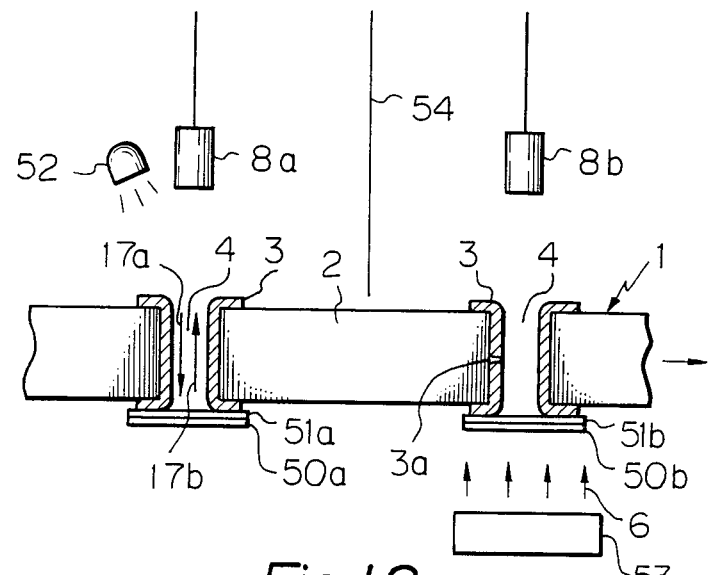
FIGS. 11 and 12 are cross-sectional diagrams of an example of an embodiment using masking means having a mirror facing one opening portion of the through hole.
Figure 12:
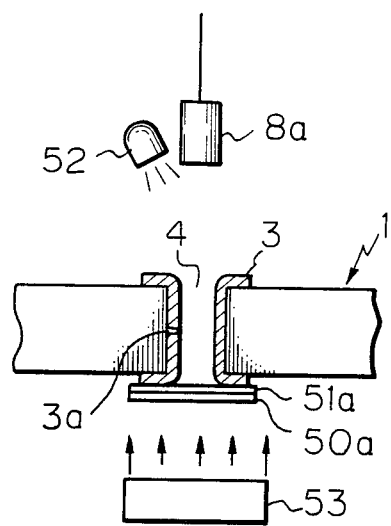

FIGS. 11 and 12 show another example of the embodiment shown in FIG. 9. As shown in FIG. 11, a light sensor 8a is provided on the side of the printed circuit board 1 opposite from a mask 50a having a mirror 51a facing the opening of the through hole 4. A light source 52 for illuminating the through hole 4 is provided near the light sensor 8a. Further, a second light sensor 8b, a second mask 50b having a mirror 51b and a light source 53 for detecting defects of the conductive layer 3 are provided at an inspecting position. The light source 53 illuminates the printed circuit board 1 through the mask 50b.

The method for inspecting the defects according to the above example will be explained below. The circuit board 1 having the through hole 4 is horizontally moved at a speed of 1 to 100 mm/sec while being radiated by the light source 52. When the through hole 4 is positioned just under the light sensor 8a, the under opening of the through hole 4 is just closed by the mask 50a with the mirror 51a facing the under opening. The light rays from the light source 52 radiate the mirror 51a through the through hole 4 and are reflected up to be detected by the light sensor 8a, with the result that the position of the through hole 4 can be determined.

Then, the through hole 4 is moved just under the light sensor 8b. When the through hole 4 is positiond just under the light sensor 8b, the under opening of the through hole 4 is closed by the mask 50b having the mirror 51b. Then, the light source 53 radiates light rays 6. Light rays leaked from a defect 3a of the conductive layer 3 are detected by light sensor 8b. If leaked the light rays are detected by the light sensor 8b, defects are present in the conductive layer 3.

It is necessary to provide a shield 54 between the light sensors 8a and 8b at a distance of about 50 mm so that light rays from the light source 52 are not detected by the light sensor 8b.

The example shown in FIG. 11 has two inspecting positions: one for detecting the existence and position of a through hole and another for detecting defects in the conductive layer. It is also possible to preform the two tasks at a single position, as shown in FIG. 12. In FIG. 12, the light sensor 8a is provided on the side of the printed circuit board 1 opposite to the mask 50a having mirror 51a. The light source 52 is also provided near the light sensor 8a. On the same side of the printed circuit board 1 as the mask 50a, there is provided a light source 53 for detecting defects 3a of the conductive layer 3.

The operation of the example shown in FIG. 12 will be explained below.

First, the printed circuit board 1 is horizontally moved. When a through hole 4 formed in the printed circuit board 1 is positioned just under the light sensor 8a. The light source 52 radiates light rays to the through hole 4. The radiated light rays are reflected by the mirror 51a and are detected by the light sensor 8a, whereby the position of the through hole 4 is detected. In the process for detecting the position of the through hole 4, the light source 53 for detecting defects of the conductive layer 3 is not switched on. After confirming the position of the through hole 4, the light source 52 is switched off and the light source 53 is switched on to detect defects 3a in the same manner as explained in FIG. 11.

Figure 13:
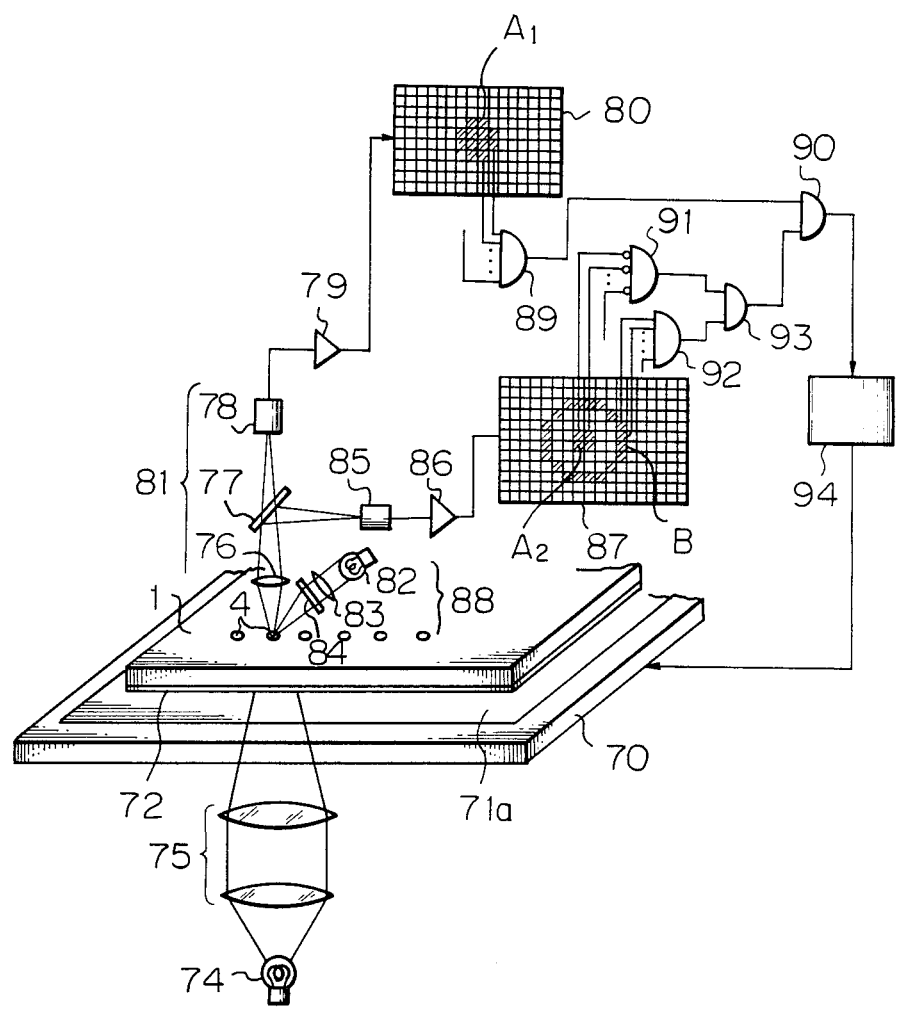
FIG. 13 is a schematic diagram of a third embodiment according to the present invention.
Figure 14A:
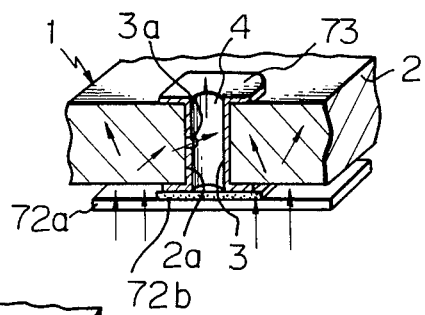
FIGS. 14A to 14C are schematic perspective diagrams of masking means used in the embodiment shown in FIG. 13.
Figure 14B:
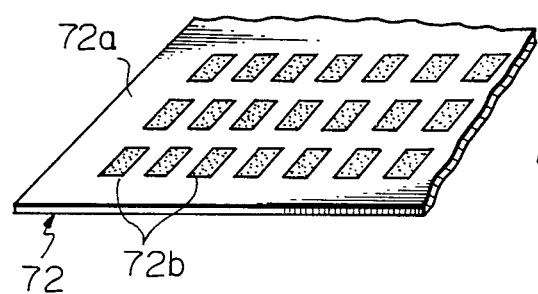

FIG. 13 shows a third embodiment of the present invention. Reference numerals 1 and 4 denote the same elements as described hereinabove. A printed-circuit-board placement portion 71a of an X-Y table stage 70 consists of a light-conducting material such as glass. On the surface of the portion 71a, there is provided a masking plate 72. The masking plate 72 is formed from a light-conducting plate 72a and an opaque portion 72b provided on the surface thereof, as shown in FIG. 14B. The arrangement of the opaque portion 72b corresponds to that of the inspected through holes. The size of the opaque portion 72b corresponds to that of the land portion 73 of a conductive layer. A light source 74 is used for radiating the printed circuit board 1 from under the X-Y stage 70. The light rays from the light source 74 are collected by an optical system 75 to radiate the printed circuit board 1 from the under surface thereof. Above the printed circuit board 1, there is provided an objective lens 76 to oppose the light source 74. The light rays leaking from a defect 3a shown in FIG. 14A pass through a filter 77 (FIG. 13) and are detected by a light sensor 78 such as TV camera or CCD. The state of the through hole 4 detected by the light sensor 78 is converted to an electric signal which is supplied to a digitizing circuit 79. The digitalizing circuit 79 transforms the converted electric signal of the aperture image of the through hole focused on the light sensor 78 to "1" or "0" corresponding to the presence of the leaked light in the through hole from the defect 3a. The digital signal has the value "1" when leaked light rays from the defect 3a are detected, and the value "0" when no such rays are detected. The digital state of the through hole 4 is memorized by a shift register 80.

Reference numeral 82 is a light source for judging the position of the through hole 4 Light rays from the light source 82 are radiated to the inspected through hole 4, through a condenser lens 83 and a filter 84 which passes light rays having different wavelengths from the filter 77. The image formation of the through hole 4 together with land portion 73 is carried out by a light sensor 85 such as a TV camera or CCD sensor. The optical image is converted to an electric signal which is supplied to digitizing circuit 86. The digitizing circuit 86 converts optical images of an opening of the through hole 4 and a land portion 73 to digital signals of "1" and "0" so that the opening of the through hole 4 in the land portion 73 is memorized by a shift register 87.

An AND gate 89 is connected to the shift register 80. The bit outputs of regions where an opening pattern $A_1$ of the through hole 4 is memorized is input to the AND gate 89. The logical product output of this AND gate 89 is added to an AND gate 90. On the other hand, a NAND gate 91 and a AND gate 92 are connected to the shift register 87. The bit outputs of regions where an opening pattern $A_2$ of the through hole 4 is memorized are input to the NAND gate 91, and the bit outputs of the regions where a boundary pattern B of the land portion 73 is memorized are input to the AND gate 92. The outputs of the NAND gate 91 and the AND gate 92 are added to the AND gate 93, and then, the output of the AND gate 93 is added to the AND gate 90. Further, the output of the AND gate 90 is added to controller 94 which controls the X-Y table 70.

The operation of the example shown in FIG. 13 will be explained. First, the masking plate 72 is adhered to the surface of the printed circuit board 1 in such a manner that the opening of the through holes 4 are closed by the opaque portion 72b. The printed circuit board 1 is then set to the X-Y table 70. The X-Y table 70 is moved to index the through hole 4 so that the through hole 4 is opposite the objective lens 76. Then, the printed circuit board 1 is partially radiated by the light source 74 through the optical system 75 and the X-Y stage 70. Additionally, the light source 82 is switched on, to partially radiate the land portion 73 through the lens 83 and the optical filter 84.

Thus, the light rays which enter from under the surface of the substrate 2 are diffused and emanate from the upper surface of the substrate 2.

When the conductive layer 3 has a defect 3a, such as a pinhole, part of the diffused light rays in the substrate 2 leak to the through hole 4 and emanate from the upper opening of the through hole 4 to the lens 76. Namely, the inner portion of the through hole 4 is lit by the light from the light source 74. An image of the upper opening of the through hole 4 is formed on the light receiving surface of the light sensor 78 through the objective lens 76 and the optical filter 77 and is converted to an electric signal. The electric signal is digitized by the digitizing circuit 79. Thus, bit outputs of the memory region of the opening pattern of the shift register 80 all become "1". Consequently, the logic condition of the AND gate 89 in which the bit outputs are input is satisfied, and the output of the AND gate 89 becomes "1".

On the other hand, when the land portion 73 of the through hole 4, indexed to the inspecting position, is radiated by the light source 82 through the condenser lens 83 and the optical filter 84, the light rays reflected on the surface of the land portion 73 are passed through the objective lens 76 and reflected by the optical filter 77 to the light sensor 85 so that the optical image is formed on the light receiving surface of the light sensor 85. Thus, the patterned optical image of the land portion 73 is converted to an electric signal, which is memorized by being digitized by the digitizing circuit 86.

Then, bit outputs corresponding to the boundary ring-shaped land portion pattern B of the shift register 87 all become "1". On the other hand, bit outputs of the memory region of the opening pattern of the through hole 4 all become "0". Thus, the logical conditions of the NAND gate 91 and the AND gate 92 are satisfied, and the logical conditions of the AND gate 93 where the two outputs of the NAND gate 91 and AND gate 92 are input are also satisfied.

Consequently, an AND condition of the AND gate 90, to which the outputs of the AND gates 89 and 93 are input is satisfied. The output is supplied to the controller 94 so that the defects in the conductive layer 3 can be found, and further the position of the defective through hole 4 can be recognized. Additionally, the controller 94 indexes the X-Y stage 70 to the next through hole 4 which is to be inspected.

When the objective lens 76 is opposes to the insulating substrate 2 under the through hole 4, the light rays from the light source 74 pass through the substrate 2 and are detected by the light sensor 78 through the objective lens 76 and optical filter 77. The light rays are then memorized by the shift register 80 and digitized by the digitizing circuit 79. Thus, an AND condition of the AND gate 89 is satisfied. However, since the condition of the position judging system means 88 for through hole 4, composed of the objective lens 76, the optical filter 77, light source 82 and light sensor 85, is not satisfied, defects of the conductive layer 3 are not determined.

When the objective lens 76 is not opposite to the through hole 4, but opposite to the conductive layer, bit outputs of the memory region matching the through hole opening pattern become "1". Thus, the output of the NAND gate 91 is held to "0", with the result that the inspection of the through hole becomes null.

When conductive layer 3 has no defects, light rays from the light source 74 do not enter the inner portion of the through hole 4 at all. Therefore, the image of the upper opening of the through hole 4 in the light sensor 78 is black. The image is digitized by the digitized circuit 79. The pattern data of the upper opening of the through hole 4, which is memorized by the shift register 80, become "0".

On the other hand, the pattern data of the land portion 73, radiated by the light source 82 through the condenser lens 83 and the optical filter 84, are the same as explained for the shift register 87, with the result that the outputs of the NAND gate 91 and the AND gate 92 become "1". Since the output of the AND gate 89 is maintained at "0", the output of the AND gate 90 is also maintained at "0", with the result that the conductive layer 3 is judged to have no defects.

According to the embodiment shown in FIG. 13, there are provided a through-hole position-judging means 88 and a defect-inspecting means 81 composed of light source 74, objective lens 76, optical filter 77 and light sensor 78. When the detecting condition in the above two means is satisfied, it can be judged that the conductive layer 3 has defects.

Figure 14C:
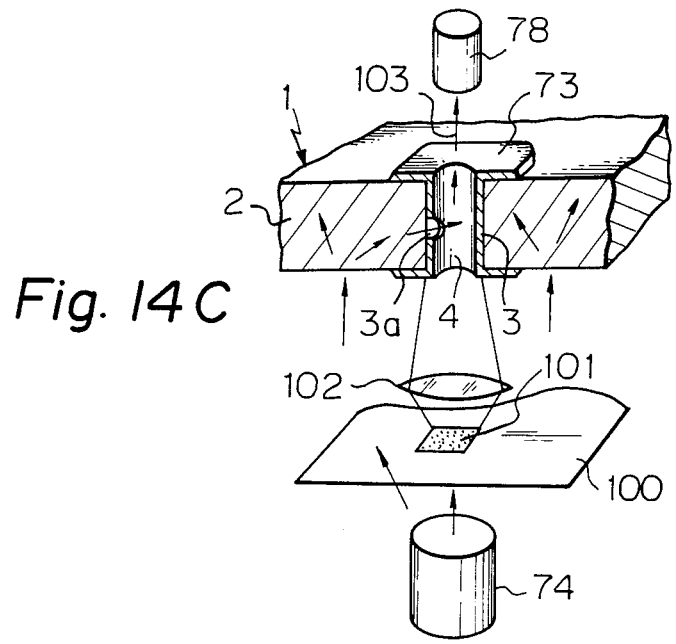

FIG. 14C is a perspective view of another example of masking means used in the apparatus shown in FIG. 13. In FIG. 14C, the masking plate 100 is provided in front of the light source 74. The masking plate 100 has at least one opaque pattern 101 in accordance with the through hole bottom opening or the land portion 73 of the conductive layer 3. A convex lens 102 is provided in front of the masking plate 100 opposed to the opaque pattern 101. The image of the opaque pattern 101 is formed by the convex lens 102 on the surface of the printed circuit board 1 in which the through hole 4 is formed so that the through hole 4 is shielded from the light rays.

The light sensor 78 for detecting the light rays 103 leaked from a defect 3a, a defect detecting means 81, and the through-hole position-judging means 88 are also provided, as shown in FIG. 13.

According to the example shown in FIG. 14C, since the masking plate 100 is not adhered to the printed circuit board 1, the masking plate 100 is not damaged or soiled. Additionally, even if the pitch and size of the through hole 4 varies, the inspection of the through hole 4 can be freely carried out by varying the position of the lens 102 or the masking plate 100 in the direction of the optical axis. In this example, the convex lens 102 may be replaced by a concave mirror. In such case, light source 74 and masking plate 100 are disposed inside of the concave mirror.

Figure 15:
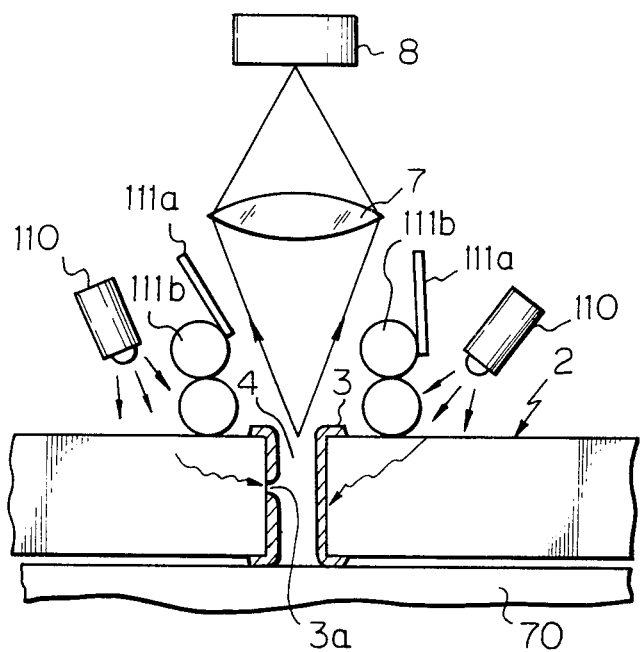
FIG. 15 is a schematic cross-sectional diagram of another embodiment of the present invention which is employed on one side of the printed circuit board.

FIG. 15 is another example of the embodiment of FIG. 13 wherein the apparatus is arranged on only one side of the printed circuit board 1 on the moving stage 70. In FIG. 15, two light sources 110 are provided to radiate one side of the printed circuit board 1. Two sets of opaque plates 111a connected to sets of opaque rolls 111b are provided on opposite sides of the through hole 4. Each set of opaque rolls 111b contacts the surface of the printed circuit board 1, the two sets of the opaque plates 111a and the two sets of opaque rolls 111b prevent light rays radiated from the light sources 110 from entering the upper opening of the through hole 4.

Therefore, if the conductive layer 3 has defects 3a, the light rays leaked from the defects 3a are detected by the light sensor 8. It is preferable that the material of the rolls 111b be rubber.

According to the present example shown in FIG. 15, since the entire apparatus is provided on one side of the printed circuit board 1, the space necessary for the apparatus is small.

Figure 16:
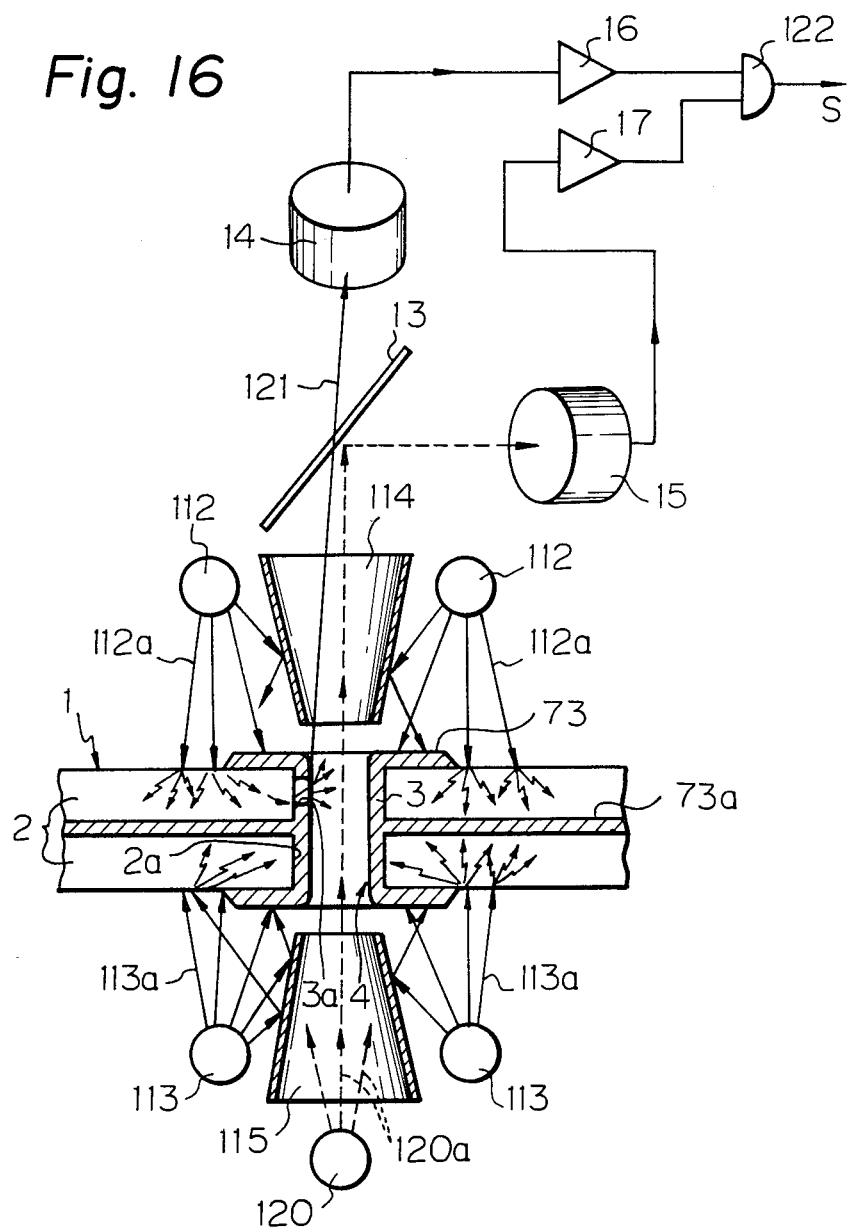
FIG. 16 is a schematic cross-sectional diagram of a fourth embodiment of the present invention.

FIG. 16 is a further embodiment of the present invention, wherein a plurality of light sources 112 and 113 are provided on both sides of the printed circuit board 1. Reference numerals 73 and 73a show a land portion and interplated layer. Red light rays are preferably radiated from the light sources 112 and 113 as they are easily transmitted through the substrate 2. Between the light sources 112 and 113 on each side of the printed circuit board 1, prisms 114 and 115, having mirror surfaces, are provided to prevent the light rays radiated from the light sources 112 and 113 from entering the through hole 4. Below the lower prism 115, a light source 120 is provided. Light rays radiated from the light source 120 pass through the lower prism 115, through hole 4, and the upper prism 114. In the light source 120, light rays having different wavelengths, such as green light rays, are preferably used. Further, an optical filter 13, light sensors 14 and 15, digitizing circuits 16 and 17, and AND circuit 122 are also provided.

The operation of the embodiment shown in FIG. 16 will be explained below. One of the through holes of the printed circuit board 1 is indexed to an inspecting position by moving the printed circuit board 1.

Red light rays 112a and 113a are radiated to both the upper and lower surfaces of the printed circuit board 1 so that the red light rays enter and diffuse in the substrate 2.

The light quantity distribution of the light rays 112a in the direction of thickness of the substrate 2 is largest at the uppermost side of the substrate 2 and gradually decreases at the lower side thereof, as shown by FIG. 17, line I.

The light quantity distribution of the light rays 113a in the direction of thickness of the substrate 2 is largest at the lowermost side of the substrate 2 and graudally decreases at the upper side thereof, as shown by FIG. 17, line II. Thus, when the substrate 2 is radiated from the light sources 112 and 113, the light quantity distribution of the light rays 112a and 113a combines as shown by FIG. 17, line III, whereby enough light for detecting defects in the conductive layer 3 can be obtained.

When the conductive layer 3 has defects 3a, part of the diffused light rays leak to the inner space of the through hole 4 and are detected by the light sensor 14 through the upper prism 114 and the filter 13, and converted to an electric signal. The signal is digitized by the digitizing circuit 16, and is then supplied to one input of the AND circuit 122.

On the other hand, when the through hole 4 is indexed to the inspecting position, the green light rays from the light sources 120 are transmitted to the lower prism 115, passed through the through hole 4, transmitted to the upper prism 114, and reflected in the direction of the light sensor 15 by the filter 13, where the green light rays 120a are inspected by the light sensor 15 and converted to an electric signal. The signal digitized by the digitizing circuit 17, is then supplied to the AND circuit 122, where the position of the through hole 4 and the defect can be detected by using the digitizing circuits 16 and 17 and the AND circuit 122, as previously mentioned in FIG. 9.

Figure 18A:
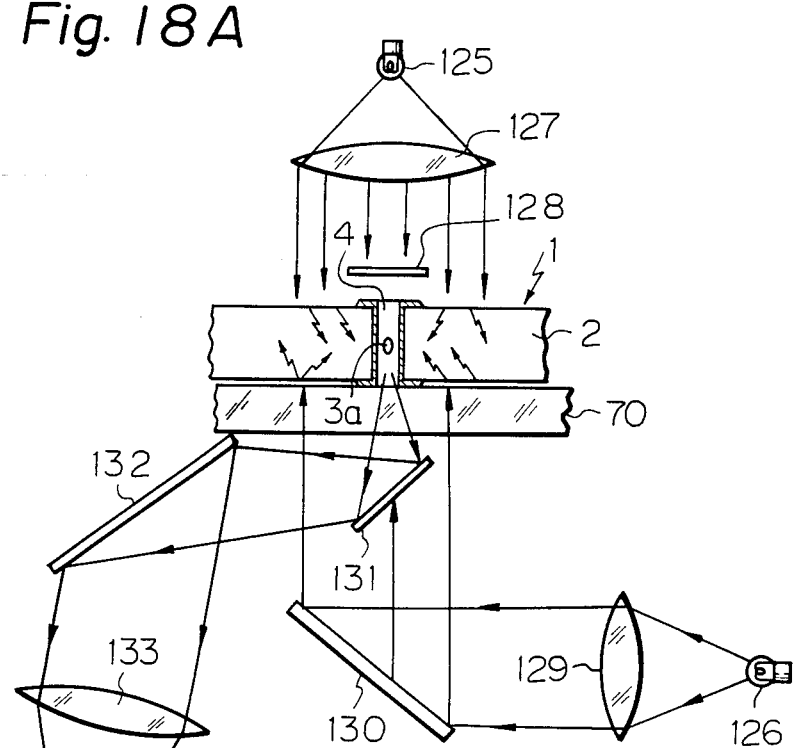
FIGS. 18A and 18B are schematic cross-sectional diagrams of other examples of the embodiment shown in FIG. 16.
Figure 18B:
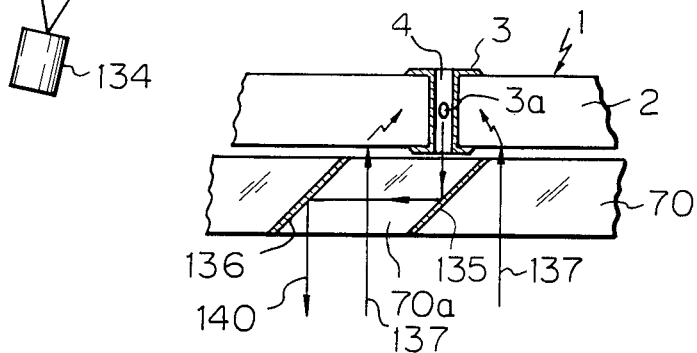

FIGS. 18A and 18B are other examples of the embodiment shown in FIG. 16. In FIG. 18A, the printed circuit board 1 having through hole 4 is provided on the X-Y stage 70. Red light rays for detecting defects radiated from a light source 125 provided above the printed circuit board 1 are passed through the lens 127 to make the rays parallel and radiate the printed circuit board 1. The upper opening of the through hole 4 is prevented from being radiated from the light source 125 by the mask 128. Light rays radiated from the source 126 for detecting defects, which light is provided on the lower side of the X-Y stage 70, are converted to parallel rays by a lens 129. The parallel rays reflected by a mirror 130 are radiated to the lower surface of the printed circuit board 1 opposite to the rays radiated from the light source 125. In the path of the light rays radiated from the light source 126 passed through the lens 129 and reflected by the mirror 130, a mirror 131 prevents the radiated light rays from entering the lower opening of the through hole 4. The same mirror 131 reflects light rays emerging from the defect 3a from the light source 125 to a mirror 132 and lens 133 to form defect images in a light sensor 134 for detecting defects.

According to the example shown in FIG. 18A, the same effect as obtained by the embodiment shown in FIG. 16 can be obtained. Additionally, since the space between the printed circuit board 1 and the light source 126 is enlarged, the X-Y stage 70, consisting of a glass plate, is provided to easily support the printed circuit board 1.

FIG. 18B shows an example for radiating the printed circuit board 1. A section 70a of the glass plate of the X-Y stage 70 is cut at a slant. In the slanted cut portions there are reflective films 135 and 136. These reflective films 135 and 136 act as reflecting means for leading light rays leaked from defects 3a, to a light sensor (not shown) for detecting defects, while the reflective film 135 acts as a mask to prevent the light rays 137 from entering the through hole 4.

FIG. 19 is a fifth embodiment of the present invention wherein the position of the defects in the conductive layer 3 can be detected.

In FIG. 19, below the lower side of the printed circuit board 1, a filter 144 for masking the lower opening of the through hole 4 is provided. The filter 144 passes light rays having a specific wavelength, such as blue light rays. Behind the filter 144, a light source 145 is provided which radiates light rays which pass through the filter 144, such as blue light rays 145b, and light rays which do not pass through the filter 144, such as red light rays. The blue light rays 145b radiated from the light source 145 pass through the filter 144, enter the through hole 4 and are used for detecting the position of the through hole 4. The red light rays 145a, partially blocked by the filter 144, are radiated to the lower surface of the substrate 2 around the through hole 4. Light sources 146 for detecting defects are provided above the upper surface of the printed circuit board 1 and radiate light rays having a different wavelength from that of the red light rays 145a, for example, green light rays, to the upper surface of the substrate 2 around the through hole 4.

A frustum-shaped opaque section 147 is positioned opposite to the upper opening of the through hole 4 in such a manner that it is surrounded by the light sources 146. The frustum-shaped section 147 prevents the light rays radiated from the light sources 146 from entering the through hole 4.

Reference numeral 7 denotes a condenser lens, 149 a filter which passes green and red light rays and reflects blue light rays, and 150 a filter which passes green light rays and reflects red light rays. On the reflective optical axis of the filter 149, a light sensor 151 is provided. The light sensor 151 detects the position of the through hole 4 by detecting the blue light rays. The output signal of light detection obtained by the light sensor 151 is supplied to one of the input terminals of a comparator 154. To the other input terminal of the comparator 154, a reference potential Vr is supplied.

On the reflective optical axis of the filter 150, a light sensor 152 is provided which detects defects positioned at the lower portion of the conductive layer 3 by detecting red light rays. On passing the optical axis of the filter 150, a light sensor 153 is provided which detects defects positioned at the upper portion of the conductive layer 3 by detecting the green light rays. The output signals of the light sensors 152 and 153 are supplied to analog/digital (A/D) converters 157 and 160 through buffer amplifiers 155 and 156, respectively. At the same time, a comparator 161, which shows positions of the defects in the through hole by comparing output signals, is connected to the A/D converters 157 and 160. The output signals $L_1$, $L_2$, $L_3$ of the comparator 161 are input to a defect position display portion 162. The comparator 161 further receives the output of the comparator 154 when the through hole 4 is detected. Furthermore, stage position information is supplied to the defect position display portion 162 from X-Y stage controlling means (not shown).

The operation of the embodiment shown in FIG. 19 will now be explained. One of through holes 4 of the printed circuit board 1 is indexed to an inspecting position by the X-Y stage (not shown). Red and blue light rays 145a and 145b and green light rays 146a are radiated to the lower and upper surfaces of the printed circuit board 1 from the light sources 145 and 146. The red light rays 145a and the green light rays 146a are diffused within the substrate 2.

The light quantity distribution of the red light rays 145a in the direction of thickness (vertical direction) of the substrate 2 is as shown by FIG. 17, line I. The light quantity distribution of the green light rays 146a in the direction of thickness (vertical direction) of the substrate 2 is as shown by FIG. 17, line II.

Blue light rays 145b, passed through the filter 144, pass through the through hole 4, are condensed by the condenser lens 7, and are reflected by the filter 149 in the direction of the light sensor 151 for detection thereby. Then, the detected blue light rays are converted to an electric signal which is supplied to the comparator 154 where it is judged if the through hole 4 is at a predetermined position. At the same time the electric signal is supplied from the comparator 154 to the comparator 161.

When a lower portion of the conductive layer 3 has a defect 3a, the red and green light rays 145a and 146a entering the substrate 2 leak to the inner portion of the through hole 4 in accordance with the light quantity distribution shown in FIG. 17 lines I and II, respectively. The red light rays 145a pass through a lens 7 and a filter 149, are reflected by the filter 150 in the direction of the light sensor 152, and are converted to an electrical signal in accordance with the light quantity by the light sensor 152. The electrical signal is amplified by the buffer amplifier 155 and converted to a digital value by the A/D converter 157.

The green light rays 146a pass through the lens 7 and filters 149 and 150, are detected by the light sensor 153, and are converted to an electrical signal in accordance with the light quantity by the light sensor 153. Then, the electrical signal is amplified by the buffer amplifier 156 and converted to a digital value by the A/D converter 160.

Since the light rays leaked from the defect 3a, positioned at a lower portion of the conductive layer 3, have a greater component of red light than that of green light, as understood from the distribution property of the quantity of light, the value of a signal A output from the A/D converter 157 is larger than that of a signal B output from the A/D converter 160. Consequently, the comparator 161 judges that the signal A is larger than the signal B. After that, the comparator 161 supplies the corresponding signal to the output line $L_1$ and subsequently to the defect position display portion 162 which shows that a lower portion of the conductive layer 3 has a defect 3a.

When an upper portion of the conductive layer 3 has a defect 3a, the quantity of green light rays 146a leaked is more than that of red light rays. Thus, the value of signal B, converted to a digital value by the A/D converter 160, is larger than that of signal A converted to a digital value by the A/D converter 157. Consequently, the comparator 161 judges that the value of signal B is larger than that of signal A and supplies a signal via the output line $L_2$ to the defect position display portion 162, which shows that an upper portion of the conductive layer 3 has a defect 3a.

When a middle portion of the conductive layer 3 has a defect 3a, the quantities of red and green light rays leaked to the inner portion of the through hole 4 equal each other. Thus, the values of signals supplied by the light sensors 152 and 153 become the same. Therefore, when the analog signals are converted to digital values by the A/D converters 157 and 160 and supplied to the comparator 161, the comparator 161 judges that signal A is substantially equal to signal B and supplies a corresponding signal via the output line $L_3$ to the defect position display portion 162, which shows that a middle portion of the conductive layer 3 has a defect 3a.

FIG. 20 is a sixth embodiment wherein permissible and unpermissible defects can be detected. In FIG. 20, reference numerals 1 to 7 denote the same elements as in preceding drawings. Above the lens 7, a plurality of light sensors 165 are provided. The light sensors 165 and the lens 7 can be moved upward and downward. Reference numeral 166 is a cover which surrounds the lens 7 and the light sensors 165.

The light sensors 165 are connected to an inspecting means which consist of digitizing circuits 168, adding circuits 169a, 169b, 169c, and 169d, and comparator 170.

The operation of the example shown in FIG. 20 will now be explained below. Light rays for detecting defects of the conductive layer 3 are radiated to the printed circuit board 1. When the conductive layer 3 has a defect 3a, part of the light rays leak from the defect 3a.

Figure 21A:
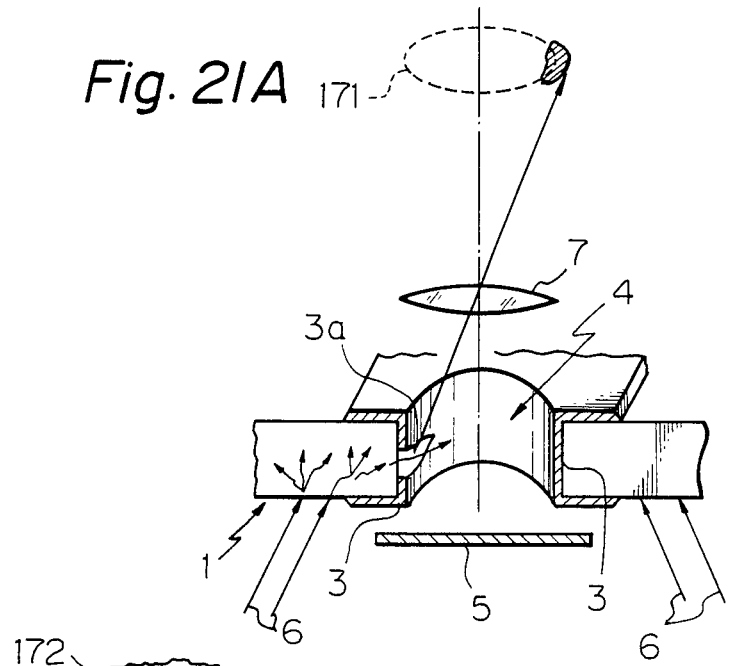
FIGS. 21A and 21B are schematic perspective views for explaining permissible defects and impermissible defects, respectively.
Figure 21B:
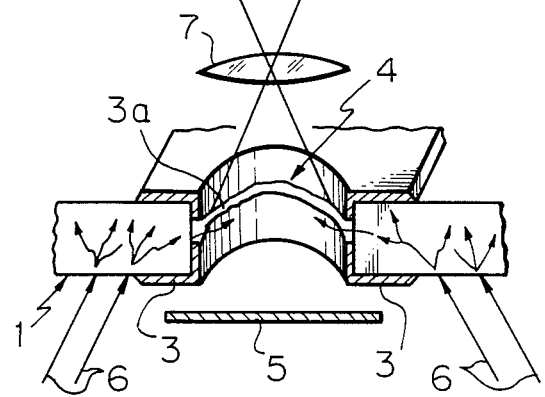

If the light sensors 165 are ring shaped, as shown in FIG. 20, they detect the defect 3a in various forms, for example, as a small point FIG. 171 which is permissible, as shown in FIG. 21A, and a ring-shaped FIG. 172, which is not permissible, as shown in FIG. 21B. The defects are separated into permissible and unpermissible defects by comparing the reference voltage Vr. No matter where the defects are in the through hole 4, they can be detected by the light sensors 165 by moving the lens 7 upward and downward.

Figure 22:
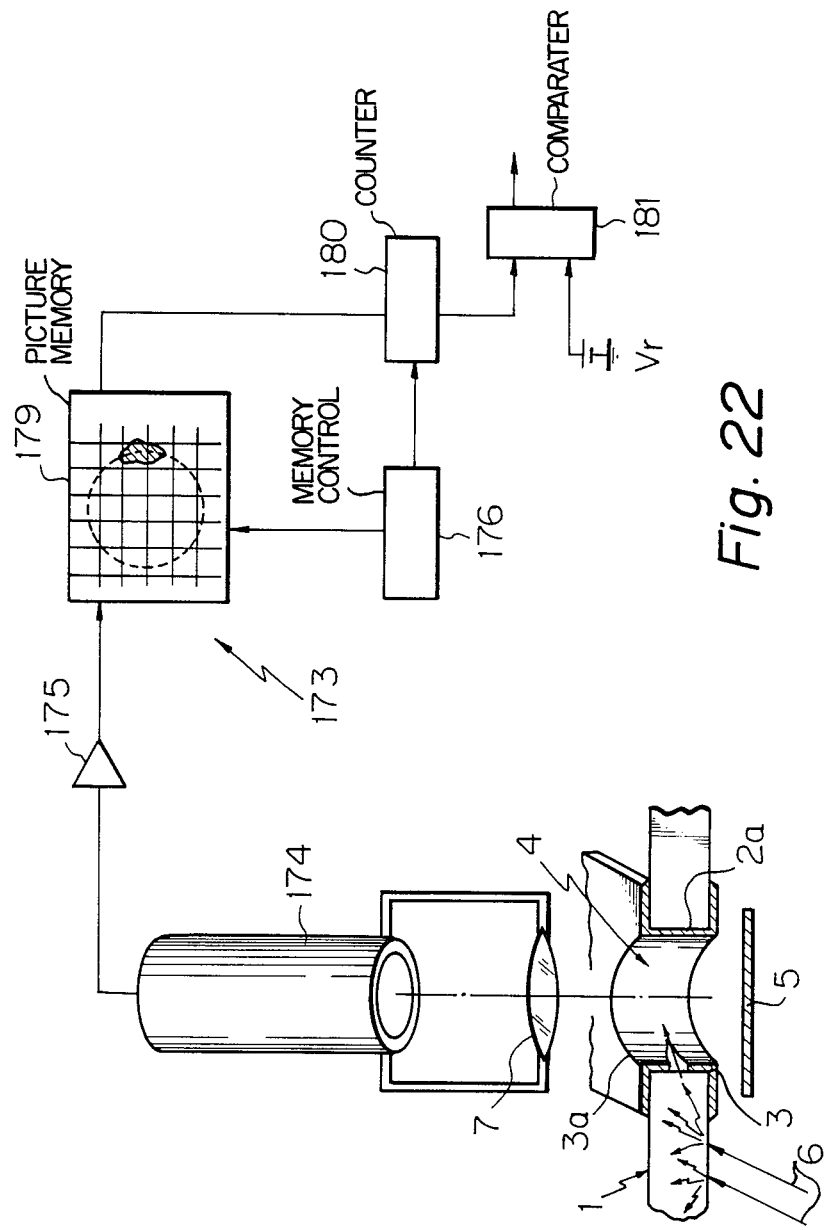
FIG. 22 is a schematic diagram of another example of the embodiment shown in FIG. 20.

FIG. 22 is another example of the embodiment shown in FIG. 20. As shown in FIG. 22, the ring-shaped light sensor shown in FIG. 20 is changed to a binary scanning means such as a TV camera or CCD sensor. The output of the detecting means 174 is connected to a digitalizing circuit 175. The output signal of the digitalizing circuit 175 is supplied to a picture memory 179 under the control of a memory control circuit 176. Then, the respective picture element signals of the picture memory 179 are supplied to a counter circuit 180 to compare it with reference voltage Vr by the comparator 181.

We claim:

1. An apparatus utilizing a light source for inspecting plated through holes in a printed circuit board made of light-conducting material, comprising:

masking means for introducing light from the light source into the interior of the printed circuit board, said masking means preventing light from directly entering the plated through holes in the printed circuit board;

means, operatively connected to receive the light from the light source, for detecting the presence of the plated through holes;

means, operatively connected to receive the light from the light source, for detecting the presence of light within the plated through holes in the printed circuit board, said detected light entering the plated through holes through defectively plated walls of the plated through holes from the interior of the printed circuit board; and means, operatively connected to said means for detecting the presence of the plated through holes and to said means for detecting the presence of light, for judging the presence of defectively plated walls of the plated through holes by signals from said detecting means for detecting the presence of the plated through holes and signals from means for detecting the presence of light within the plated through holes in the printed circuit board.

2. An apparatus according to claim 1, wherein said masking means comprises an opaque mask.

3. An apparatus according to claim 2, wherein said opaque mask comprises felt.

4. An apparatus according to claim 1, wherein said masking means comprises liquid crystal.

5. An apparatus according to claim 1, wherein said masking means comprises a rotating cylindrical mask.

6. An apparatus according to claim 1, wherein said masking means comprises a disc rotating mask.

7. An apparatus according to claim 1, wherein said masking means is located a predetermined distance from one of the plated through holes.

8. An apparatus according to claim 1, wherein said masking means comprises an optical filter for passing light having a specified wavelength.

9. An apparatus according to claim 1, wherein said masking means is operatively connected to the light source for inspecting the plated through holes.

10. An apparatus according to claim 1, wherein said masking means comprises a mirror facing the plated through holes.

11. An apparatus according to claim 1, wherein the light is introduced from both sides of the printed circuit board, the quantity of distribution of the light which is diffused in the printed circuit board being substantially uniform in the printed circuit board.

12. An apparatus according to claim 11, wherein said masking means comprises conical and cylindrical means.

13. An apparatus according to claim 1, wherein the light source and said masking means are located at the same side of the printed circuit board.

14. An apparatus according to claim 13, wherein said masking means comprises opaque rolls.

15. An apparatus according to claim 1, wherein said means for detecting the presence of the plated through holes comprises:
a light source for irradiating the plated through holes;
a lens for condensing the light for irradiating the plated through holes; and
a light sensor operatively connected to receive the light irradiating the plated through holes.

16. An apparatus according to claim 1, wherein said means for detecting the presence of light within the plated through holes in the printed circuit board comprises:

a lens for condensing the light within the plated through holes; and
a light sensor for detecting the light within the plated through holes.

17. An apparatus according to claim 1, wherein said means for determining the presence of a defectively plated wall of the plated through holes comprises:
first logic means, operatively connected to said means for detecting the presence of the plated through holes, for producing a first logic value;
second logic means, operatively connected to said means for detecting the light from the defectively plated wall of the plated through holes, for producing a second logic value; and
determining means, operatively connected to said first and second logic means, for determining a combination of logic values obtained by said first logic means and said second logic means.

18. An apparatus according to claim 17, wherein said first and second logic means each comprise:
a shift register; and
a comparator operatively connected to said shift register.

19. An apparatus according to claim 17, wherein said determining means comprises an AND gate.

20. An apparatus utilizing light sources for inspecting plated through holes in a printed circuit board having first and second sides and made of light-conducting material, comprising:
masking means for introducing light from the light sources into the interior of the printed circuit board, said masking means located at the first and second sides of the printed circuit board and preventing light from directly entering the plated through holes in the printed circuit board, the light sources being located at the first and second sides of the printed circuit board, and respective light from the light sources located at the first and second sides of the printed circuit board having different wavelengths;
means, operatively connected to receive the light from the light sources, for detecting the presence of the plated through holes;
means, operatively connected to receive the light from the light sources, for detecting the presence of the respective light within the plated through holes in the printed circuit board, the detected light entering the plated through holes, through defectively plated walls of the plated through holes, from the interior of the printed circuit board; and
means, operatively connected to said means for detecting the presence of the respective light, for determining the position of defectively plated walls of the plated through holes.

21. An apparatus according to claim 20, wherein said masking means located at the first side of the printed circuit board is a frustum-shaped conical masking means and wherein said masking means located at the second side of the printed circuit board is a flat plate light filter.

22. An apparatus according to claim 20, wherein the light source located at the first side of the printed circuit board is a source of green light and the light source located at the second side of the printed circuit board is a source of red light.

23. An apparatus according to claim 20, wherein said means for detecting the presence of the plated through holes comprises:

a source of light for irradiating the plated through holes;

a lens for receiving and condensing the light irradiating the plated through holes; and a light sensor operatively connected to receive the condensed light.

24. An apparatus according to claim 23, wherein the light source for irradiating the plated through holes is a source of blue light.

25. An apparatus according to claim 20, wherein said means for detecting the presence of light within the plated through holes in the printed circuit board comprises:

a lens for receiving and condensing light within the plated through holes;

a first light filter, operatively connected to receive the condensed light, for filtering the condensed light; and a first light sensor operatively connected to receive the filtered light.

26. An apparatus according to claim 25, wherein said means for detecting the presence of respective light within the plated through holes in the printed circuit board further comprises:

a second light filter, operatively connected to receive the filtered light from said first light filter, for filtering the filtered light from said first light filter; and second and third light sensors, respectively, operatively connected to receive the filtered light from said first and second light filters.

27. An apparatus according to claim 20, wherein said means for determining the position of defectively plated walls of the plated through holes comprises:

first logic means, operatively connected to said means for detecting the presence of the plated through holes, for producing a first logic output signal;

second logic means, operatively connected to said means for detecting the presence of the printed circuit board, for producing a second logic output signal; and defect position display means, operatively connected to said first and second logic means, for displaying the position of the defectively plated walls of the plated through holes in the printed circuit board.

28. An apparatus according to claim 27, wherein said first and second logic means comprise comparators.

29. An apparatus utilizing a light source for inspecting plated through holes in printed circuit boards made of light-conducting material, comprising:

masking means for introducing light from the light source into the interior of the printed circuit boards, said masking means preventing light from directly entering the plated through holes in the printed circuit boards;

means for detecting the presence of the plated through holes;

means for detecting the image of light within the plated through holes in the printed circuit boards and outputting output signals, the detected light entering the plated through holes from the interior of the printed circuit boards;

means, operatively connected to said means for detecting the image of the plated through holes and to said means for detecting the light source, for determining the degree of defects of the defectively plated walls of the plated through holes.

30. An apparatus according to claim 29, wherein said means for detecting the image of light with the plated through holes in the printed circuit boards comprises means, having a ring type shape, for detecting the image in parts.

31. An apparatus according to claim 29, wherein said means for determining the degree of defects of defectively plated walls of the through holes comprises:

logic means, operatively connected to receive the output signals supplied from said means for detecting the image of light within the plated through holes in the printed circuit boards, for producing output logic values;

adding means, operatively connected to said logic means, for adding the output logic values;

a comparator operatively connected to said adding means; and reference value means operatively connected to said comparator.

32. A method of inspecting a printed circuit board made of light-conducting material for detecting defectively plated through holes, comprising the steps of:

(a) introducing light into the printed circuit board;

(b) confirming the presence of the plated through holes by detecting the light within the plated through holes to obtain a display signal of the presence of the plated through holes;

(c) detecting the presence of light within the plated through holes to obtain display signals of the presence of defectively plated walls of the plated through holes, the light from the plated through holes arriving through defectively plated walls of the plated through holes;

(d) displaying a defect signal in accordance with the display signal of the presence of the plated through holes and the display signals of the presence of a defectively plated wall of the plated through holes.

33. A method of inspecting a printed circuit board made of light-conducting material for detecting defectively plated through holes, comprising the steps of:

(a) introducing light into the printed circuit board;

(b) confirming the presence of the plated through holes by detecting the light within the plated through holes to obtain display signals of the presence of the plated through holes;

(c) masking the plated through holes with a masking material;

(d) detecting the presence of light within the plated through holes, the light entering the plated through holes through defectively plated walls of the plated through holes;

(e) displaying a defect signal in accordance with the display signal of the presence of the plated through holes and the display signal of the presence of defectively plated walls of the plated through holes.

* * * * *

UNITED STATES PATENT AND TRADEMARK OFFICE
CERTIFICATE OF CORRECTION

PATENT NO. : 4,560,273

DATED : DECEMBER 24, 1985

INVENTOR(S) : MORITOSHI ANDO ET AL.

It is certified that error appears in the above-identified patent and that said Letters Patent is hereby corrected as shown below:

```
Col. 2, line 35, "unpermissible" should be --impermissible--;
        line 64, "source" should be --sources--.

Col. 3, line 39, "of indicating" should be --indicating the--.

Col. 4, line 2, "gram" should be --grams--;
        line 5, "gram" should be --grams--;
        line 25, "," should be --;--.

Col. 6, line 42, delete "mask";
        line 42, after "crystal" insert --mask--.

Col. 7, line 20, "aa" should be --a--.

Col. 9, line 1, delete "just";
        line 13, delete "the".

Col. 10, line 3, "digitalizing" should be --digitizing--;
         line 13, after "4" insert --.--;
         line 20, after "to" insert --a--.
```

UNITED STATES PATENT AND TRADEMARK OFFICE
CERTIFICATE OF CORRECTION

PATENT NO. : 4,560,273

DATED : DECEMBER 24, 1985

INVENTOR(S) : MORITOSHI ANDO ET AL.

It is certified that error appears in the above-identified patent and that said Letters Patent is hereby corrected as shown below:

Col. 11, line 24, after "input" insert --,--;
        line 27, after "input" insert --,--;
        line 33, "opposes" should be --opposite--.

Col. 13, line 58, delete "light".

Col. 16, line 25, "unpermissible" should be --impermissible--;
        line 46, "unpermissible" should be --impermissible--.

Signed and Sealed this

Thirteenth Day of May 1986

[SEAL]

Attest:

Attesting Officer

DONALD J. QUIGG

Commissioner of Patents and Trademarks